(12) United States Patent
Ko et al.

(10) Patent No.: US 12,011,487 B2
(45) Date of Patent: Jun. 18, 2024

(54) SALVIANOLIC ACID-GELATIN CONJUGATE HYDROGEL PARTICLES

(71) Applicant: Nano and Advanced Materials Institute Limited, Hong Kong (CN)

(72) Inventors: Chun Hay Ko, Hong Kong (CN); Joo Ann Ewe, Hong Kong (CN); Guang Rong Tan, Singapore (SG); Hok Him Pan, Hong Kong (CN); Tsz Wai Ng, Hong Kong (CN)

(73) Assignee: Nano and Advanced Materials Institute Limited, Hong Kong (CN)

( * ) Notice: Subject to any disclaimer, the term of this patent is extended or adjusted under 35 U.S.C. 154(b) by 183 days.

(21) Appl. No.: 17/206,273

(22) Filed: Mar. 19, 2021

(65) Prior Publication Data

US 2021/0308279 A1  Oct. 7, 2021

Related U.S. Application Data

(60) Provisional application No. 63/006,137, filed on Apr. 7, 2020.

(51) Int. Cl.
| | | |
|---|---|---|
| *A61K 47/69* | (2017.01) | |
| *A61K 9/00* | (2006.01) | |
| *A61K 31/216* | (2006.01) | |
| *A61K 31/343* | (2006.01) | |
| *A61K 47/18* | (2017.01) | |
| *A61K 47/22* | (2006.01) | |
| *B82Y 5/00* | (2011.01) | |
| *B82Y 30/00* | (2011.01) | |
| *B82Y 40/00* | (2011.01) | |

(52) U.S. Cl.
CPC ........ *A61K 47/6939* (2017.08); *A61K 9/0053* (2013.01); *A61K 31/216* (2013.01); *A61K 31/343* (2013.01); *A61K 47/18* (2013.01); *A61K 47/22* (2013.01); *B82Y 5/00* (2013.01); *B82Y 30/00* (2013.01); *B82Y 40/00* (2013.01)

(58) Field of Classification Search
CPC .............. A61K 47/6939; A61K 9/0053; A61K 31/216; A61K 31/343; A61K 47/18; A61K 47/22; A61K 9/5161; A61K 47/6435; B82Y 5/00; B82Y 30/00; B82Y 40/00
See application file for complete search history.

(56) References Cited

U.S. PATENT DOCUMENTS

| | | | |
|---|---|---|---|
| 10,226,417 | B2 | 3/2019 | Jarrett et al. |
| 2019/0177787 | A1 | 6/2019 | Fonnum et al. |

FOREIGN PATENT DOCUMENTS

KR  20190081507 A  7/2019

OTHER PUBLICATIONS

Yinrong Phytochemistry p. 117 (Year: 2002).*
Ma, Salvianolic Acids Review, Front. Pharmacol. pp. 1-13, Feb. 2019.*
Li, Salviae miltiorrhizae Radix et Rhizoma, J. Cromatogr. 1216, p. 1941. Dec. 2008.*
Shi, Polysaccharides, Intl. J. of Biol. Macromolecules, p. 37, Jul. 2016.*

* cited by examiner

*Primary Examiner* — Sarah Alawadi
*Assistant Examiner* — Thurman Wheeler
(74) *Attorney, Agent, or Firm* — S&F/WEHRW

(57) ABSTRACT

The present disclosure relates to salvianolic acid-gelatin conjugate load retentive hydrogel nanoparticles useful for oral delivery of salvianolic acid, pharmaceutical compositions comprising the same, and methods of use and preparation thereof.

8 Claims, 10 Drawing Sheets

Salvianolic acid A

Salvianolic acid B

Salvianolic acid C

Salvianolic acid D

| Chemicals | Expt. 1 | Expt. 2 | Expt. 3 |
|---|---|---|---|
| Salvianolic acid B (g) | 0.1 | 0.1 | 0.1 |
| EDC (g) | 0.4 | 0.4 | 0.4 |
| NHS (g) | 0.6 | 0.6 | 0.6 |
| Gelatin (g) | 0.3 | 0.1 | 0.01 |
| Water (mL) | 45 | 900 | 90 |
| PBS 10X (mL) | 5 | 100 | 10 |
| Yield (%)* | 48.5 | 65.3 | 79.1 |
| Precipitate formed | Dark brown fragments  | Light brown powder  | Light brown powder  |
| Solubility | X | √ | √ |

| FORMULATION NUMBER | API | | CORE | INNER SHELL | | OUTER SHELL | |
|---|---|---|---|---|---|---|---|
| | TYPE | CONC. | CORE TYPE | Agarose | Alginate | Chitosan | Shellac |
| SAB-03 | Salvianolic acid B | 1.5 WT.% | Gelatin | 0.50% | - | - | - |
| SAB-05 | | | Gelatin | 0.25% | 0.25% | - | - |
| SAB-06 | | | Gelatin | 0.50% | - | 3% | - |
| SAB-08 | | | Gelatin | 0.50% | - | - | 3% |

FIG. 8

| | Released amount of Salvianolic acid B at pH 1.0 (stomach acid) | Released amount of Salvianolic acid B at pH 6.8 (intestinal fluid) |
|---|---|---|
| SAB-03 | 62.5 ± 1.21% | 87.6 ± 0.21% |
| SAB-05 | 80.2 ± 2.14% | 88.9 ± 1.93% |
| SAB-06 | 28.4 ± 0.91% | 85.4 ± 1.77% |
| SAB-08 | 20.2 ± 0.67% | 90.4 ± 0.62% |

FIG. 9

SALVIANOLIC ACID-GELATIN CONJUGATE HYDROGEL PARTICLES

CROSS-REFERENCE TO RELATED APPLICATIONS

This application claims the benefit of priority of U.S. Provisional Application No. 63/006,137, filed on Apr. 7, 2020, the contents of which being hereby incorporated by reference in their entirety for all purposes.

TECHNICAL FIELD

The present disclosure relates to salvianolic acid-gelatin conjugate load retentive hydrogel nanoparticles useful for oral delivery of salvianolic acid, pharmaceutical compositions comprising the same, and methods of use and preparation thereof.

BACKGROUND

Salvianolic acids are major bioactive constituents of the traditional Chinese medicinal herb, *Salvia miltiorrhiza*, and are known to exhibit several therapeutic properties, such as anti-oxidant properties, anti-cancer, anti-inflammatory and cardioprotective properties. However, the development of therapeutic treatments using salvianolic acids has been hampered by their poor properties. Salvianolic acids are extremely hydrophilic compounds with low permeabilities, and as a result also have poor oral bioavailabilities.

Hydrogel particles have been widely used in food and beverage, personal care, cosmetics and pharmaceuticals for active ingredient encapsulation and delivery. Microencapsulation of active ingredients in hydrogel particles can improve bioavailability, enables controlled/targeted release and can enhance stability by stabilizing the active ingredient.

Despite the many advantages afforded by encapsulation in hydrogel particles, leakage of hydrophilic active ingredients limits the use of hydrogel particles in aqueous formulations. In this respect, hydrogel-forming natural polymers include proteins, such as collagen and gelatin and polysaccharides, such as starch, alginate, and agarose, which are typically hydrophilic in nature, but do not immobilize hydrophilic agents in the hydrogel matrix. Consequently, current hydrogel particles loaded with hydrophilic agents, such as salvianolic acids, can be unstable in aqueous conditions.

Accordingly, there exists a need to develop improved salvianolic acid drug delivery systems that address or overcomes at least some of the issues raised above.

SUMMARY

In a first aspect provided herein is a nanoparticle comprising a core and a polymer shell coating the core, wherein the polymer shell comprises an inner shell comprising a polysaccharide and optionally an outer shell comprising chitosan, shellac, or an enteric coating material, wherein the core comprises a salvianolic acid-gelatin conjugate comprising gelatin covalently bonded to salvianolic acid.

In a first embodiment of the first aspect, provided herein is the nanoparticle of the first aspect, wherein the salvianolic acid-gelatin conjugate is represented by Formula 1, 2, 3, or 4:

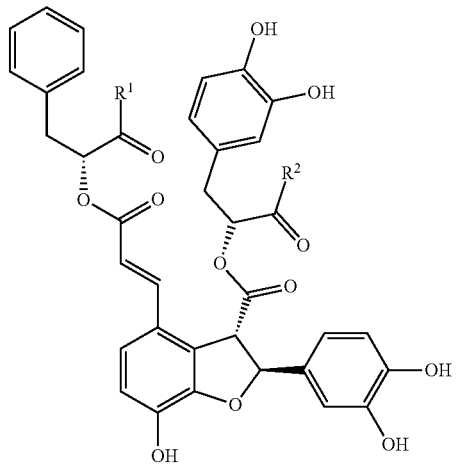

1

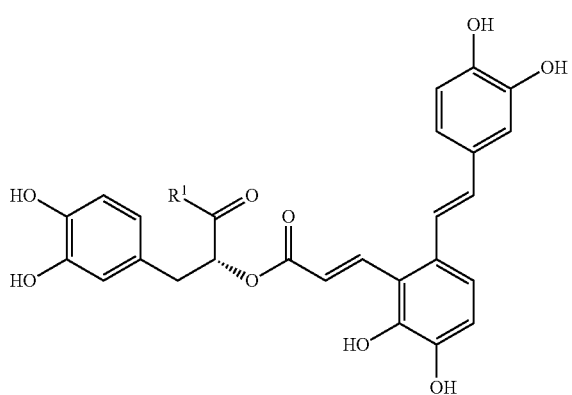

2

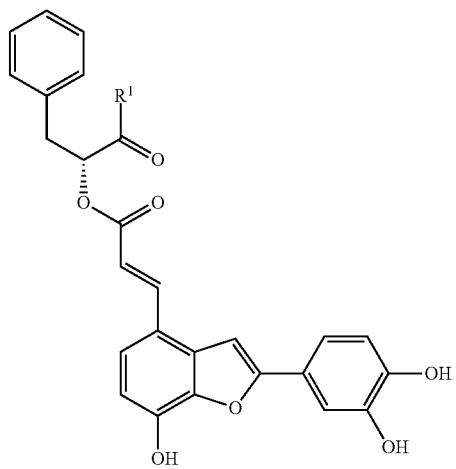

3

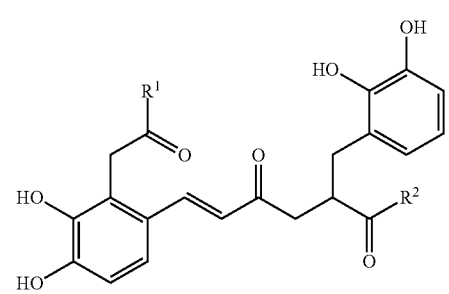

4 or a pharmaceutically acceptable salt thereof, wherein R¹ and R² are independently selected from the group consisting of OH and —NHR³;

and R³ for each instance is independently an amine containing amino acid side chain of the gelatin or an N-terminal amine of the gelatin, with the proviso that at least one of R¹ or R² is —NHR³.

In a second embodiment of the first aspect, provided herein is the nanoparticle of the first aspect, wherein the polysaccharide is selected from the group consisting of alginate, agarose, hyaluronic acid, carboxymethyl cellulose, hydroxypropyl methylcellulose, carrageenan, collagen, dextran, dextran sulfate, chondroitin sulfate, dermatan sulfate, chitin, chitosan, heparan, heparan sulfate, and combinations thereof.

In a third embodiment of the first aspect, provided herein is the nanoparticle of the first aspect, wherein the polysaccharide is alginate, agarose, or a combination thereof.

In a fourth embodiment of the first aspect, provided herein is the nanoparticle of the first aspect, wherein the enteric coating material is selected from the group consisting of an anionic copolymer derived from methacrylic acid and ethyl acrylate, hydroxypropyl methylcellulose phthalate, polyvinyl acetate phthalate, polyvinyl acetate phthalate, cellulose acetate phthalate, or a combination thereof.

In a fifth embodiment of the first aspect, provided herein is the nanoparticle of the first aspect, wherein the outer shell comprises chitosan or shellac.

In a sixth embodiment of the first aspect, provided herein is the nanoparticle of the first aspect, wherein the salvianolic acid is represented by Formula 1; the polysaccharide is alginate, agarose, or a combination thereof; and the second polymer comprises chitosan or shellac.

In a second aspect, provided herein is a pharmaceutical composition comprising the nanoparticle of the first aspect and at least one pharmaceutically acceptable excipient.

In a third aspect, provided herein is a method of treating cancer, inflammatory or a cardiac disease in a subject in need thereof comprising administering a therapeutically effective amount of the nanoparticle of the first aspect to the subject.

In a fourth aspect, provided herein is a method of preparing the nanoparticle of the first aspect, the method comprising: contacting gelatin, a salvianolic acid, a coupling agent, and optionally a coupling additive thereby forming the salvianolic acid-gelatin conjugate; coating the salvianolic acid-gelatin conjugate with the polysaccharide thereby forming an inner shell coated gelatin conjugate; and optionally coating the inner shell coated gelatin conjugate with chitosan, shellac, or an enteric coating material thereby forming the nanoparticle of the first aspect.

In a first embodiment of the fourth aspect, provided herein is the method of the four aspect, wherein the polysaccharide is selected from the group consisting of alginate, agarose, hyaluronic acid, carboxymethyl cellulose, hydroxypropyl methylcellulose, carrageenan, collagen, dextran, dextran sulfate, chondroitin sulfate, dermatan sulfate, chitin, chitosan, heparan, heparan sulfate, and combinations thereof.

In a second embodiment of the fourth aspect, provided herein is the method of the fourth aspect, wherein the enteric coating material is selected from the group consisting of an anionic copolymer derived from methacrylic acid and ethyl acrylate, hydroxypropyl methylcellulose phthalate, polyvinyl acetate phthalate, polyvinyl acetate phthalate, cellulose acetate phthalate, or a combination thereof.

In a third embodiment of the fourth aspect, provided herein is the method of the fourth aspect, wherein the salvianolic acid-gelatin conjugate represented by Formula 1:

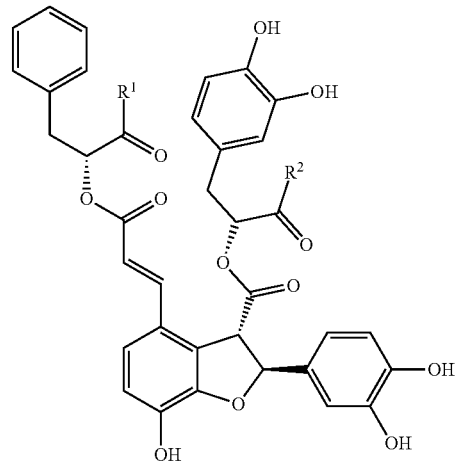

or a pharmaceutically acceptable salt thereof, wherein R¹ and R² are independently selected from the group consisting of OH and —NHR³; and R³ for each instance is independently an amine containing amino acid side chain of the gelatin or a N-terminal amine of the gelatin, with the proviso that at least one of R¹ or R² is —NHR³.

In a fourth embodiment of the fourth aspect, provided herein is the method of the third embodiment of the fourth aspect, wherein the coupling agent is 1-ethyl-3-(3-dimethylaminopropyl)carbodiimide (EDC); and the coupling additive is N-hydroxysuccinimide (NHS).

In a fifth embodiment of the fourth aspect, provided herein is the method of the third embodiment of the fourth aspect, wherein the gelatin and the salvianolic acid are present in a mass ratio between 3:1 to 1:10, respectively.

In a sixth embodiment of the fourth aspect, provided herein is the method of the fourth embodiment of the fourth aspect, wherein the EDC, gelatin and the salvianolic acid are present in a mass ratio between 4:3:1 to 40:1:10, respectively.

In a seventh embodiment of the fourth aspect, provided herein is the method of the fourth aspect, wherein the polysaccharide is selected from the group consisting of alginate, agarose, or a combination thereof; and the acid-gelatin conjugate and the polysaccharide are present in a mass ratio of 1:4 to 99:1, respectively.

In an eighth embodiment of the fourth aspect, provided herein is the method of the fourth aspect, wherein the inner shell coated gelatin conjugate and the chitosan, shellac, or an enteric coating material are present in a mass ratio of 1:4 to 99:1, respectively.

In a ninth embodiment of the fourth aspect, provided herein is the method of the sixth embodiment of the fourth aspect, wherein the polysaccharide is selected from the group consisting of alginate, agarose, or a combination thereof; and the acid-gelatin conjugate and the polysaccharide are present in a mass ratio of 7:3 to 4:1, respectively.

In a tenth embodiment of the fourth aspect, provided herein is the method of the ninth embodiment of the fourth aspect, wherein the inner shell coated gelatin conjugate and the chitosan or shellac are present in a mass ratio of 7:3 to 4:1, respectively.

Other aspects and advantages of the present invention will be apparent to those skilled in the art from a review of the ensuing description.

BRIEF DESCRIPTION OF THE DRAWINGS

The above and other objects and features of the present invention will become apparent from the following description of the invention, when taken in conjunction with the accompanying drawings, in which:

FIG. 8 depicts the composition of various nanoparticles according to certain embodiments described herein.

FIG. 9 depicts experimental results for release of salvianolic acid B from the nanoparticles described in FIG. 8 under conditions that simulate the pH in stomach acid and intestinal fluid.

DETAILED DESCRIPTION

Definitions

Figure 1:
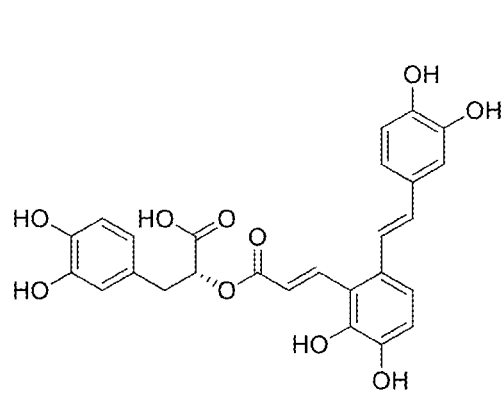
FIG. 1 depicts the chemical structures of salvianolic acid A, B, C, and D.
Figure 1:
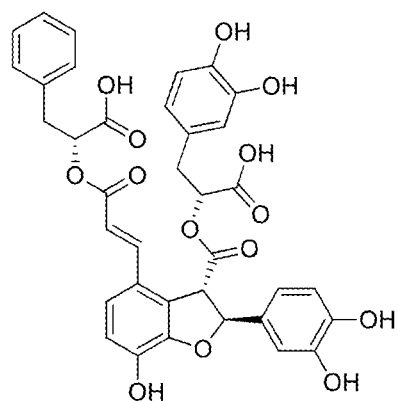
Figure 1:
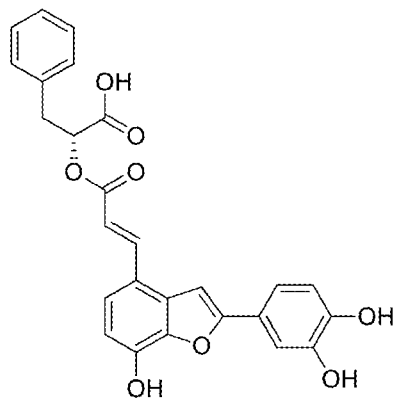
Figure 1:
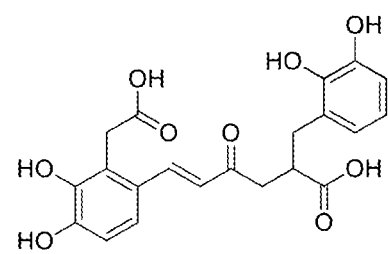

The term "pharmaceutically acceptable salt" or "salt" refers to a salt of one or more compounds. Suitable pharmaceutically acceptable salts of compounds include acid addition salts which may, for example, be formed by mixing a solution of the compound with a solution of a pharmaceutically acceptable acid, such as hydrochloric acid, hydrobromic acid, sulfuric acid, fumaric acid, maleic acid, succinic acid, benzoic acid, acetic acid, citric acid, tartaric acid, phosphoric acid, carbonic acid, or the like. Where the compounds carry one or more acidic moieties, pharmaceutically acceptable salts may be formed by treatment of a solution of the compound with a solution of a pharmaceutically acceptable base, such as lithium hydroxide, sodium hydroxide, potassium hydroxide, tetraalkylammonium hydroxide, lithium carbonate, sodium carbonate, potassium carbonate, ammonia, alkylamines, or the like. Pharmaceutically acceptable salts can also include zwitterions.

The term "pharmaceutically acceptable carrier" refers to a medium that is used to prepare a desired dosage form of a compound. A pharmaceutically acceptable carrier can include one or more solvents, diluents, or other liquid vehicles; dispersion or suspension aids; surface active agents; isotonic agents; thickening or emulsifying agents; preservatives; solid binders; lubricants; and the like. Remington's Pharmaceutical Sciences, Fifteenth Edition, E. W. Martin (Mack Publishing Co., Easton, Pa., 1975) and Handbook of Pharmaceutical Excipients, Third Edition, A. H. Kibbe ed. (American Pharmaceutical Assoc. 2000), disclose various carriers used in formulating pharmaceutical compositions and known techniques for the preparation thereof.

The term "therapeutically effective amount" as used herein, means that amount of active compound or pharmaceutical agent that elicits a biological or medicinal response in a cell culture, tissue system, animal, or human that is being sought by a researcher, veterinarian, clinician, or physician, which includes alleviation of the symptoms of the disease, condition, or disorder being treated.

The term "subject" as used herein, refers to an animal, typically a mammal or a human, that will be or has been the object of treatment, observation, and/or experiment. When the term is used in conjunction with administration of a compound or drug, then the subject has been the object of treatment, observation, and/or administration of the compound or drug.

As used herein, and as well understood in the art, "treatment" is an approach for obtaining beneficial or desired results, including clinical results, Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

Where the use of the term "about" is before a numerical value, the present teachings also include the specific numerical value itself, unless specifically stated otherwise. As used herein, the term "about" refers to a ±10%, ±7%, ±5%, ±3%, ±1%, or ±0% variation from the numerical value unless otherwise indicated.

Provided herein is a nanoparticle comprising a core and a polymer shell coating the core, wherein the polymer shell comprises an inner shell comprising a polysaccharide and optionally an outer shell comprising chitosan, shellac, or an enteric coating material, wherein the core comprises a salvianolic acid-gelatin conjugate comprising gelatin covalently bonded to a salvianolic acid.

The salvianolic acid can be a salvianolic acid A, salvianolic acid B, salvianolic acid C, salvianolic acid D, or a combination thereof. FIG. 1 depicts the chemical structures of Salvianolic acids A, B, C, and D.

Salvianolic acids contain one or two carboxylic acids that can be reacted with the amines present in gelatin in the presence of a coupling agent and optionally a coupling agent additive thereby forming the salvianolic acid-gelatin conjugate.

The salvianolic acid-gelatin conjugate can be represented by the compounds of Formula 1, 2, 3, or 4:

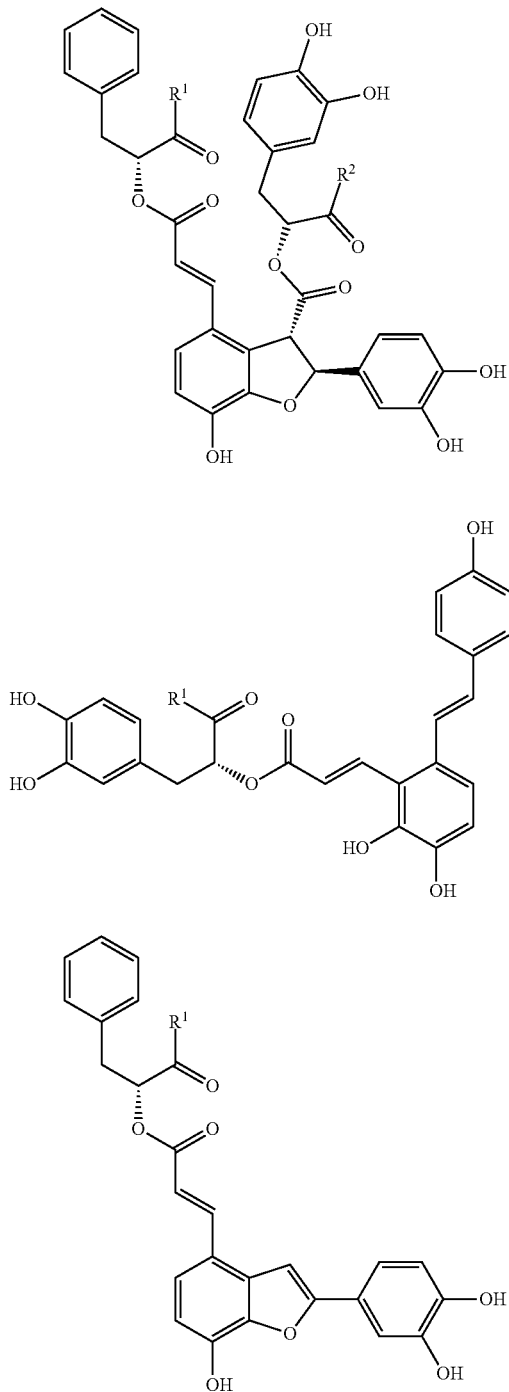

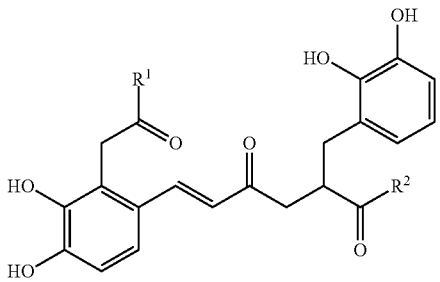

or a pharmaceutically acceptable salt thereof, wherein $R^1$ and $R^2$ are independently selected from the group consisting of OH and —$NHR^3$; and $R^3$ for each instance is independently an amine containing amino acid side chain of the gelatin or an N-terminal amine of the gelatin, with the proviso that in compounds of Formula 1 and 4 at least one of $R^1$ or $R^2$ is —$NHR^3$ and that in the compounds of Formula 2 and 3 $R^1$ is —$NHR^3$.

In instances in which both $R^1$ and $R^2$ are —$NHR^3$ in the compounds of Formula 1 and 4, each $R^3$ can be the same gelatin molecule or two different gelatin molecules.

Figure 2:
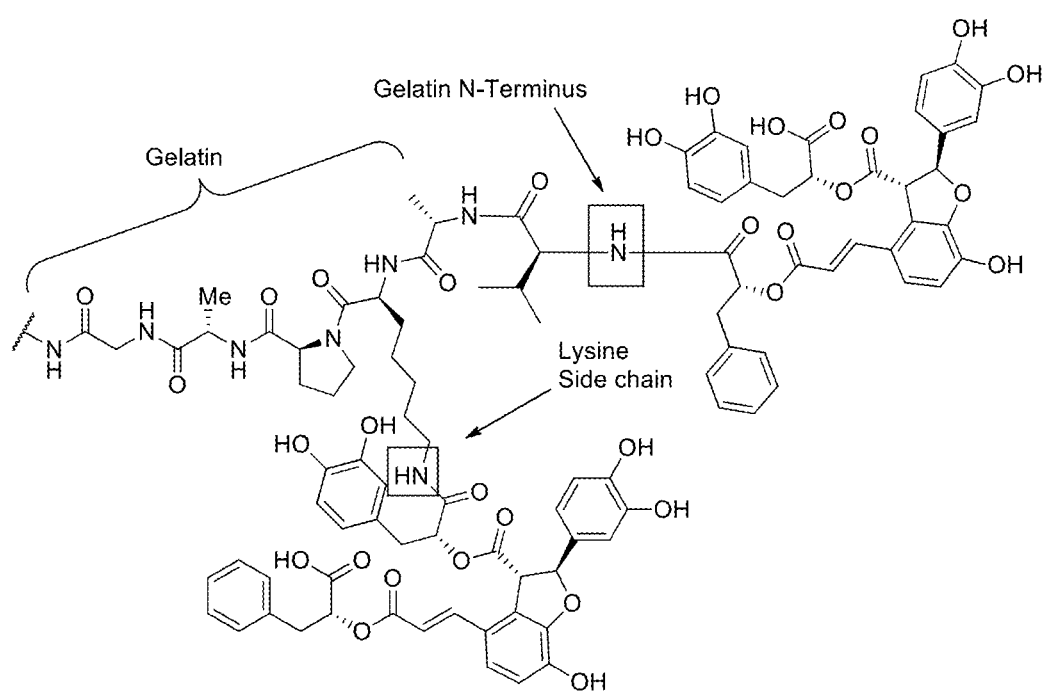
FIG. 2 depicts an exemplary simplified chemical structure of a salvianolic acid-gelatin conjugate according to certain embodiments described herein.
Figure 3:
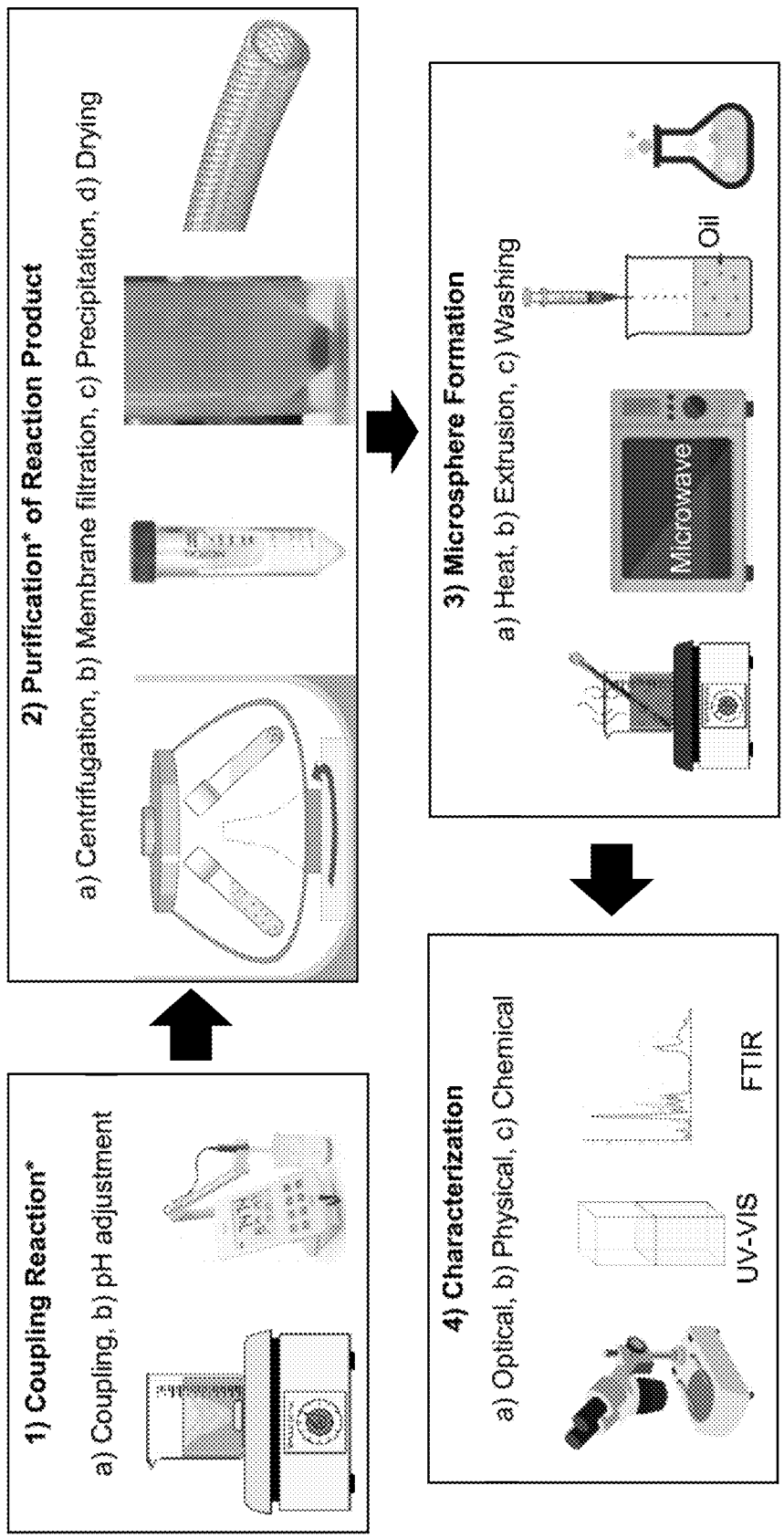
FIG. 3 depicts an exemplary procedure and apparatuses for preparing, purifying, and characterizing the nanoparticles described herein.
Figure 4:
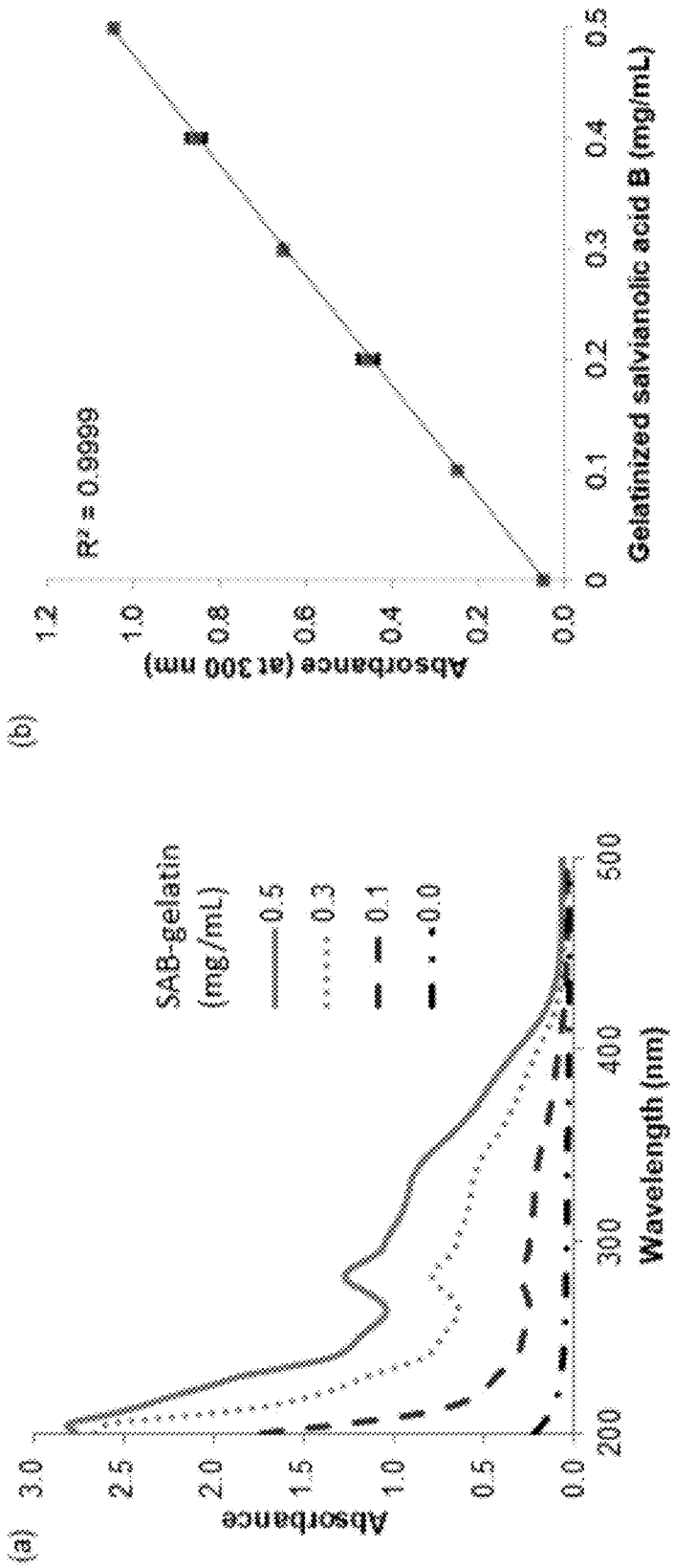
FIG. 4 depicts the (A) absorbance spectrum and (B) calibration curve of a salvianolic acid-gelatin conjugate according to certain embodiments described herein as measured by using the UV-Vis light spectrophotometer, n=3.
Figure 5:
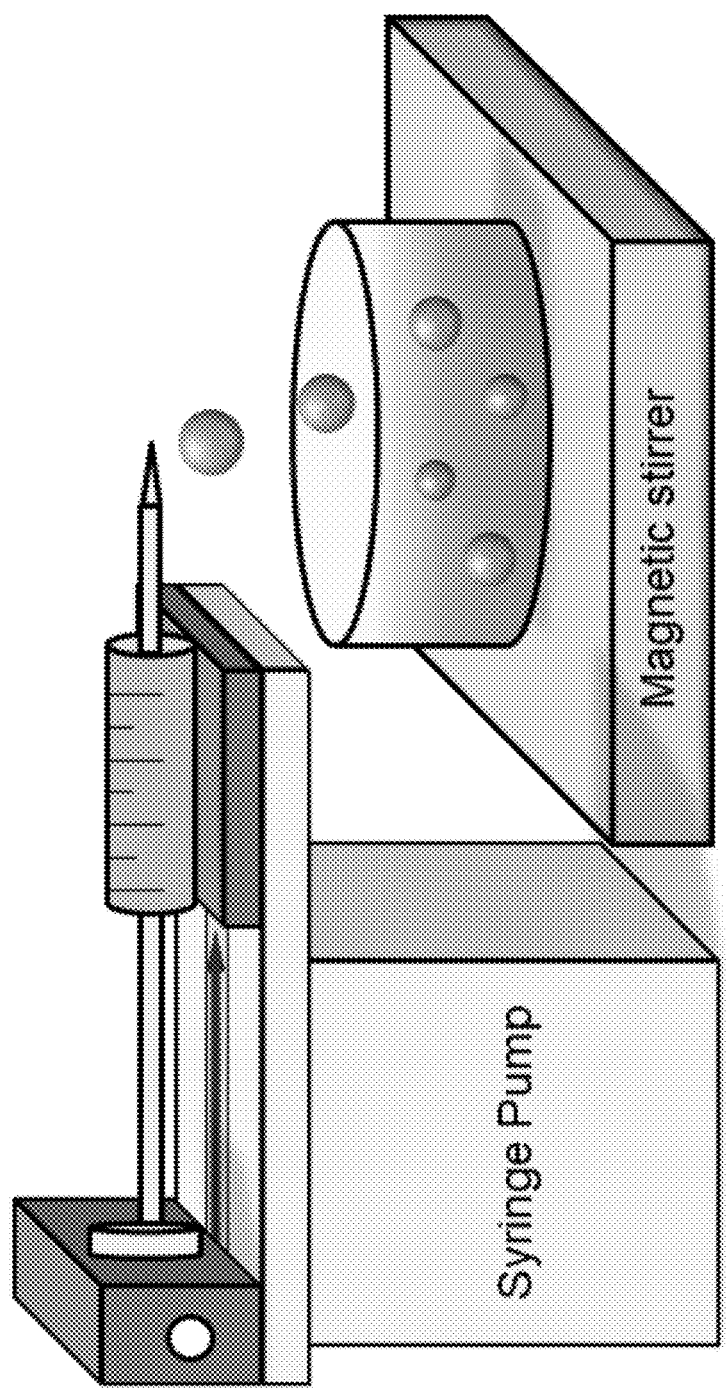
FIG. 5 depicts a schematic illustration of an exemplary system for preparing the nanoparticles described herein. Microsphere formation can be accomplished by using an extrusion method. A syringe pump injects an extrudate containing a salvianolic acid-gelatin conjugate mixture into a liquid solution, wherein particle formation occurs. The extrudate can comprise, for example, the salvianolic acid-gelatin conjugate and the polysaccharide or the inner shell coated gelatin conjugate and chitosan, shellac, or an enteric coating material. The liquid solution can comprise olive oil or aqueous calcium chloride.

FIG. 2 depicts a simplified structure of an exemplary salvianolic acid B-gelatin conjugate (compounds of Formula 1) showing two molecules of salvianolic acid B covalently bonded to the amine of a lysine side chain and the N-terminus of the gelatin.

In instances in which the salvianolic acid contains two carboxylic acids one or both carboxylic acids can be covalently bonded to gelatin. When two carboxylic acids of salvianolic acid are covalently bonded to gelatin, they can be covalently bonded intramolecularly to one gelatin polymer or intermolecularly crosslinking two gelatin polymers.

Amines present in gelatin that can be covalently bonded to salvianolic acid can be amines present in side chains of amino acids, such as lysine and the N-terminal amine of gelatin. The amount of lysine in gelatin can vary depending on the source of the gelatin, but typically represents about 3-5% of the amino acids in gelatin. In certain embodiments, substantially all of the amino groups in the lysine side chains are covalently bonded to the salvianolic acid.

Under certain conditions other functional groups, besides amines, present in gelatin may undergo reaction with salvianolic acid in the coupling reaction. Such functional groups include hydroxyl, guanidinyl, thioyl, and seleonyl functional groups present in side chains of naturally occurring amino acids present in gelatin. Such conjugates are also contemplated by the present disclosure.

The gelatin molecules present in the salvianolic acid-gelatin conjugate may comprise 1, 2, 3, 4, 5, 6, 7, 8, 9, 10 or more molecules of salvianolic avid covalently bonded therein. In certain embodiments, the gelatin molecules present in the salvianolic acid-gelatin conjugate may be crosslinked by the salvianolic acid. Crosslinking can occur intramolecularly within the same gelatin polymer or intermolecularly between two gelatin polymers.

In certain embodiments, the nanoparticle described herein comprises the salvianolic acid-gelatin conjugate of Formula 1.

The salvianolic acid-gelatin conjugate is covered by an inner shell comprising a polysaccharide. Exemplary polysaccharides include, but are not limited to starch, alginic acid, agarose, hyaluronic acid, carboxymethyl cellulose, hydroxypropyl methylcellulose, carrageenan, collagen, dextran, dextran sulfate, chondroitin sulfate, dermatan sulfate, chitin, chitosan, heparan, heparan sulfate, or conjugate salts there and/or combination thereof.

In certain embodiments, the polysaccharide is alginic acid, agarose, or a combination thereof. The alginic acid may be present as its conjugate salt, i.e., as a metal alginate. In such cases, alginate may comprise a cation selected from the Group I or Group II metals. In certain embodiments, the alginate is sodium alginate, magnesium alginate, or calcium alginate.

The nanoparticle can comprise the salvianolic acid-gelatin conjugate and the inner shell in a mass ratio of 1:99 to 99:1, respectively. In certain embodiments, the nanoparticle comprises the salvianolic acid-gelatin conjugate and the inner shell in a mass ratio of 1:9 to 99:1; 1:4 to 99:1; 3:7 to 99:1; 2:3 to 99:1; 1:1 to 99:1; 3:2 to 99:1; 7:3 to 99:1; 4:1 to 99:1; 9:1 to 99:1, respectively. In certain embodiments, the nanoparticle comprises the salvianolic acid-gelatin conjugate and the inner shell in a mass ratio of 1:1 to 9:1; 3:2 to 4:1; 3:2 to 4:1; or 7:3 to 4:1, respectively. In certain embodiments, the nanoparticle comprises the salvianolic acid-gelatin conjugate and the inner shell in a mass ratio of 3:1, respectively.

Table 1 shows the formulation of an exemplary nanoparticle comprising a salvianolic acid B-gelatin conjugate (SAB-gelatin) in accordance with certain embodiments described herein and a comparative nanoparticle comprising core consisting of an admixture of salvianolic acid B and gelatin.

TABLE 1

Formulation of the hydrogel particle loaded with salvianolic acid B (SAB) only or with SAB-gelatin conjugate.

| Formulation | API | API Conc. | Core Material | Shell Material |
|---|---|---|---|---|
| SAB - gelatin conjugate-loaded hydrogel particle | SAB-gelatin | 1.5% | Gelatin | Agarose (0.5%) |
| SAB-loaded hydrogel particle | SAB only | 1.5% | Gelatin | Agarose (0.5%) |

Table 2 shows the improvement in load retention of salvianolic acid B in the nanoparticle comprising salvianolic acid B-gelatin conjugate (SAB-gelatin) in accordance with certain embodiments described herein compared and a comparative nanoparticle comprising core consisting of an admixture of salvianolic acid B and gelatin.

TABLE 2

Enhancement of load retention of load retention of salvianolic acid B (SAB) in the nanoparticles described herein SAB as measured by UV-Vis spectrophotometer.

| Formulation | Batch No. | Loading | Mean ± SD |
|---|---|---|---|
| SAB-gelatin conjugate-loaded hydrogel particle | 1 | 82.7% | 80.9 ± 2.1% |
| | 2 | 77.9% | |
| | 3 | 82.0% | |
| SAB-loaded hydrogel particle | 1 | Below detection limit of UV-Vis Spectrophotometer | |

Figure 6:
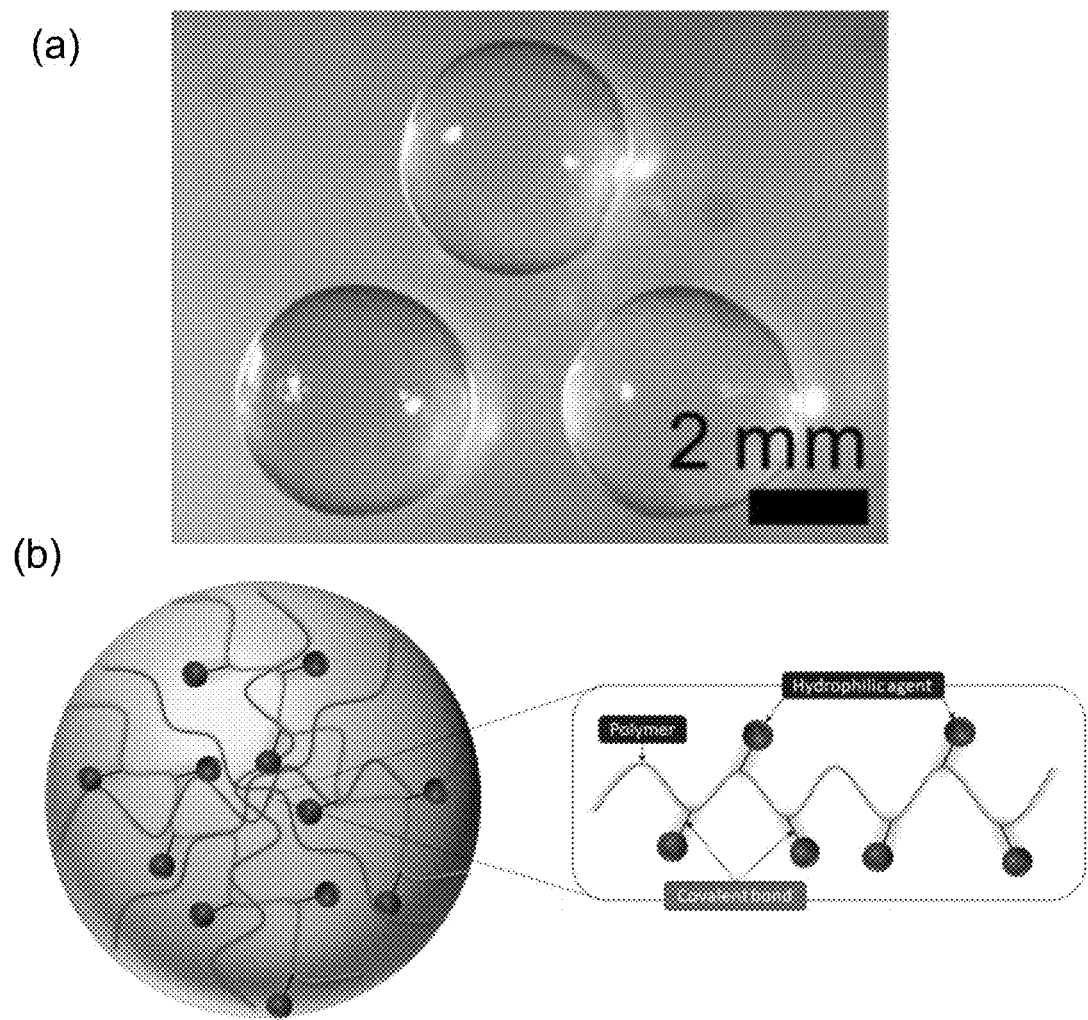
FIG. 6 depicts (A) a light microscopy photograph of nanoparticle according to certain embodiments described; and (B) a schematic showing the structure of the nanoparticle, the matrix covalently bound with hydrophilic agents (i.e., salvianolic acid). The window showing a schematic of the hydrophilic agent (salvianolic acid)-gelatin conjugate.

FIG. 6A shows light microscopy image of the nanoparticles described herein having a substantially spherical structure with an average particle diameter of about 2.5-3.00 mm.

The salvianolic acid-gelatin conjugate can optionally comprise an outer shell comprising chitosan, shellac, or an enteric coating material, wherein the outer shell is coated on the surface of the inner shell.

Exemplary enteric coatings include, but are not limited to, Eudragit L-30-D 55 (an anionic copolymer derived from methacrylic acid and ethyl acrylate), hydroxypropyl methylcellulose phthalate HP50 (HPMCP-HP50) (USP/NF 220824), HP55 (HPMCP-HP55) (USP/NF type 200731) and HP55S available from Shin Etsu Chemical, Coateric™ (polyvinyl acetate phthalate) (Colorcon Ltd.), Sureteric™ (polyvinyl acetate phthalate) (Colorcon, Ltd.), or Aquateric™ (cellulose acetate phthalate) (FMC Corp.) and the like.

In certain embodiments, the outer shell comprises chitosan, shellac, or a combination thereof.

The nanoparticle can comprise the inner shell coated gelatin conjugate and the outer shell coating in a mass ratio of 1:99 to 99:1, respectively. In certain embodiments, the nanoparticle comprises the inner shell coated gelatin conjugate and the outer shell coating in a mass ratio of 1:9 to 99:1; 1:4 to 99:1; 3:7 to 99:1; 2:3 to 99:1; 1:1 to 99:1; 3:2 to 99:1; 7:3 to 99:1; 4:1 to 99:1; 9:1 to 99:1, respectively. In certain embodiments, the nanoparticle comprises the inner shell coated gelatin conjugate and the outer shell coating in a mass ratio of 1:1 to 9:1; 3:2 to 4:1; 3:2 to 4:1; or 7:3 to 4:1, respectively. In certain embodiments, the inner shell coated gelatin conjugate and the outer shell are present in the aqueous solution in a mass ratio of 3:1, respectively.

The nanoparticle can comprise the salvianolic acid-gelatin conjugate and the outer shell in a mass ratio of 1:9 to 9:1, respectively. In certain embodiments, the nanoparticle comprises the inner shell coated gelatin conjugate and the outer shell coating in a mass ratio of 1:9 to 4:1; 1:9 to 7:7; 1:9 to 3:2; 1:9 to 1:1; 1:4 to 1:1; or 1:4 to 2:3, respectively. In certain embodiments, the nanoparticle comprises the inner shell coated gelatin conjugate and the outer shell coating in a mass ratio of 1:2, respectively.

The nanoparticle can comprise the salvianolic acid-gelatin conjugate between 20-40% by weight; the inner shell between 5-20% by weight; and the outer shell between 40-75% by weight In certain embodiments, the nanoparticle comprises the salvianolic acid-gelatin conjugate between 25-35% by weight; the inner shell between 5-15% by weight; and the outer shell between 50-70% by weight; or the salvianolic acid-gelatin conjugate between 28-32% by weight; the inner shell between 8-12% by weight; and the outer shell between 56-64% by weight. In certain embodiments, the nanoparticle comprises the salvianolic acid-gelatin conjugate about 30% by weight; the inner shell between about 10% by weight; and the outer shell about 60% by weight.

Figure 7:
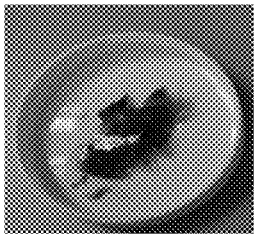
FIG. 7 depicts experimental conditions and results for preparing the salvianolic acid-gelatin conjugate according to certain embodiments described herein.
Figure 7:
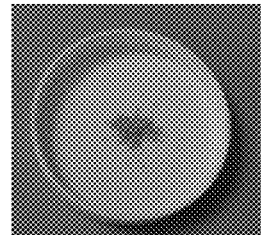
Figure 7:
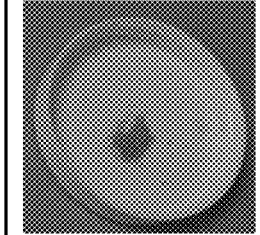

FIG. 8 shows the composition of nanoparticles SAB-03, SAB-05, SAB-06, and SAB-08 prepared using the salvianolic acid-gelatin conjugate prepared in accordance with Experiment 3 in FIG. 7. The nanoparticles are prepared using different inner shell and optionally outer shell materials. The release profile of SAB-03, SAB-05, SAB-06, and SAB-08 are shown in FIG. 9. The data suggests that SAB-08 releases the smallest amount of the salvianolic acid B under simulated stomach acid conditions and the highest release of salvianolic acid B in the intestinal fluid, which suggests that SAB-08 would protect the majority of the salvianolic acid B in SAB-08 from stomach acid and provide the highest targeted delivery of salvianolic acid B to the intestinal track.

Figure 10:
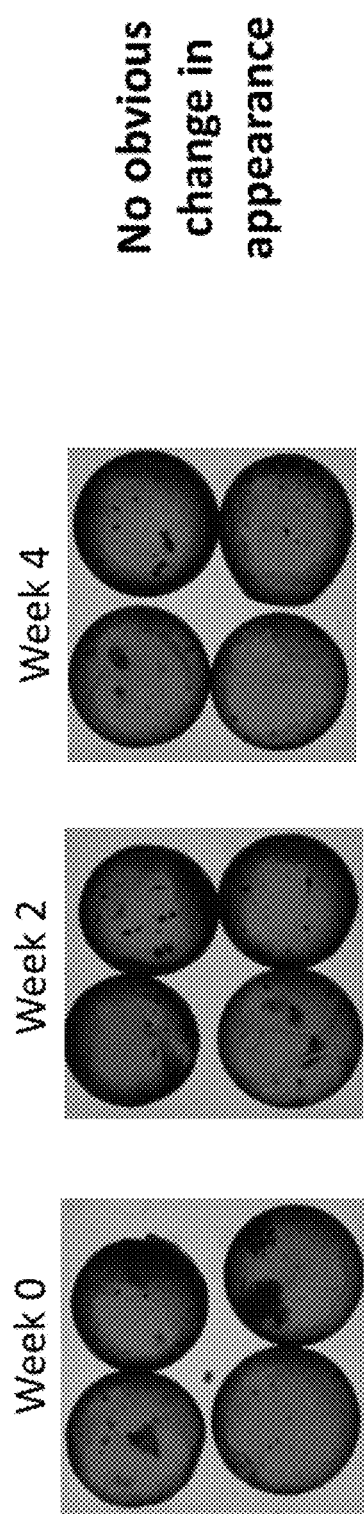
FIG. 10 depicts light microscopy photographs of SAB-08 nanoparticles at 0, 2, and 4 weeks and shows that there is no substantial changes in the appearance of the nanoparticles, which suggests the nanoparticles are stable.
Figure 11:
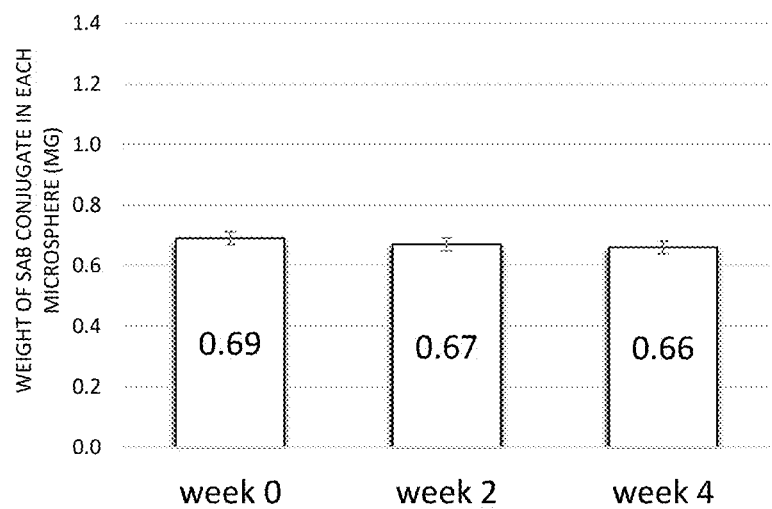
FIG. 11 depicts a table showing the change in weight of SAB-08 nanoparticles at 0, 2, and 4 weeks. No substantial change in weight of the nanoparticles suggests that the nanoparticles are stable.

The stability of SAB-08 over a period of four weeks is shown in the series of light microscopy images shown in FIG. 10, which show no obvious changes in appearance. FIG. 11 shows a minor change in weight over the same 4 week period of SAB-08 nanoparticles. These results suggest that the nanoparticles described herein are stable.

The present disclosure also provides a pharmaceutical composition comprising a nanoparticle described herein and at least one pharmaceutically acceptable excipient.

The nanoparticles described herein and their pharmaceutically acceptable salts can be administered to a subject either alone or in combination with pharmaceutically acceptable carriers or diluents in a pharmaceutical composition according to standard pharmaceutical practice. The nanoparticles can be administered orally or parenterally. Parenteral administration includes intravenous, intramuscular, intraperitoneal, subcutaneous and topical, the preferred method being intravenous administration.

Accordingly, the present disclosure provides pharmaceutically acceptable compositions, which comprise a therapeutically-effective amount of one or more of the nanoparticles described herein, formulated together with one or more pharmaceutically acceptable carriers (additives) and/or diluents. The pharmaceutical compositions of the present disclosure may be specially formulated for administration in solid or liquid form, including those adapted for the following: (1) parenteral administration, for example, by subcutaneous, intramuscular, intravenous or epidural injection as, for example, a sterile solution or suspension, or sustained-release formulation; and (2) oral administration, for example, drenches (aqueous or non-aqueous solutions or suspensions), tablets, e.g., those targeted for buccal, sublingual, and systemic absorption, boluses, powders, granules, pastes for application to the tongue.

As set out herein, certain embodiments of the salvianolic acid-gelatin conjugates described herein may contain a basic functional group, such as amino, and are, thus, capable of forming pharmaceutically acceptable salts with pharmaceutically-acceptable acids. The term "pharmaceutically acceptable salts" in this respect, refers to the relatively non-toxic, inorganic and organic acid addition salts of the salvianolic acid-gelatin conjugates of the present disclosure. These salts can be prepared in situ in the administration vehicle or the dosage form manufacturing process, or by separately reacting a purified salvianolic acid-gelatin conjugates of the invention in its free base form with a suitable organic or inorganic acid, and isolating the salt thus formed during subsequent purification. Representative salts include the hydrobromide, hydrochloride, sulfate, bisulfate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

The pharmaceutically acceptable salts of the salvianolic acid-gelatin conjugates of the present disclosure include the conventional nontoxic salts or quaternary ammonium salts of the compounds, e.g., from nontoxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the salvianolic acid-gelatin conjugates described herein may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of the salvianolic acid-gelatin conjugates described herein. These salts can likewise be prepared in situ in the administration vehicle or the dosage form manufacturing process, or by separately reacting the purified salvianolic acid-gelatin conjugates described herein in their free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives, solubilizing agents, buffers and antioxidants can also be present in the compositions.

The nanoparticles described herein can be prepared using well known synthetic techniques. The salvianolic acid-gelatin conjugate can be prepared by coupling the salvianolic acid with gelatin using a coupling reaction mediated by a coupling agent and optionally a coupling agent additive.

The coupling agent can be a carbodiimide, such as DCC, DIC, EDC, CIC, BMC, CPC, BDDC, PIC, PEC, and BEM, a uranium/aminium salt, such as HATU, HBTU, TATU, TBTU, HAPyU, TAPipU, HAPipU, HBPipU, HAMBU, HBMDU, HAMTU, 5,6-B(HATU), 4,5-B(HATU), HCTU, TCTU, and ACTU, phosphonium salts, such as AOP, BOP, PyAOP, PyBOP, PyOxm, PyNOP, PyFOP, NOP, and PyClock, immonium salts, such as BOMI, BDMP, BMMP, BPMP, and AOMP.

The additive can be any coupling additive known in the art, such as HOBt, 6-NO$_2$-HOBt, 6-Cl-HOBt, 6-CF$_3$-HOBt, HOAt, HODhbt, HODhat, NHS, and Oxyma.

In certain embodiments, the coupling agent is EDC and the coupling additive is NHS.

The gelatin and the salvianolic acid can be present in the coupling reaction at a mass ratio of 3:1 to 1:10, respectively. In certain embodiments, the gelatin and the salvianolic acid are present in the coupling reaction at a mass ratio of 1:1 to 1:10.

The coupling agent, gelatin, and the salvianolic acid can be used in the coupling reaction of 4:3:1 to 40:1:10 or 4:1:1 to 40:1:10, respectively.

The coupling agent, coupling agent additive, gelatin, and the salvianolic acid can be used in the coupling reaction in a mass ratio of 4:6:3:1 to 40:60:1:10 or 4:6:1:1 to 40:60:1:10, respectively.

The coupling reaction between the gelatin and salvianolic acid can be conducted in any polar protic or aprotic solvent. In certain embodiments, the coupling reaction solvent is water, alcohols, ketones, ethers, haloalkanes, or combinations thereof. In certain embodiments, the solvent is water, dichloromethane, 1,2-dichloroethane, chloroform, tetrahydrofuran, diethyl ether, acetone, 1,4-dioxane, acetonitrile, ethyl acetate, propylene carbonate, ethanol, isopropanol, and combinations thereof.

In certain embodiments, the coupling reaction between the gelatin and salvianolic acid is conducted in water. The water can be pH buffered between a pH of 7.2 to 8.0. In certain embodiments, the coupling reaction between the gelatin and the salvianolic acid is conducted in phosphate buffered saline at a pH between 7.2 and 8.0.

The coupling reaction between the gelatin and salvianolic acid can be conducted at 0° ° C. to 60° C. In certain embodiments, the coupling reaction between the gelatin and salvianolic acid is conducted at 10° C. to 60° C.; 20° ° C. to 60° C.; 20° C. to 50° C.; 20° C. to 40° C.; be or 20° C. to 30° C. In certain embodiments, the coupling reaction between the gelatin and salvianolic acid is conducted at room temperature.

FIG. 7 shows the results of coupling salvianolic acid B with gelatin using EDC and NHS. The results of these experiments suggest that coupling yields and product properties improve when the gelatin and salvianolic acid B are present in a mass ratio of 1:1 to 1:10, respectively. In Experiment 1: the precipitate was dark brown fragments; the fragments formed were due to excess amounts of gelatin; the fragments were insoluble in hot water and could not be granulated. In Experiment 2: the precipitate was light brown powder; the yield was higher than Experiment 1; and required prolong purification process (3 hr) to harvest all precipitate due to high reaction volume. In Experiment 3: The precipitate was light brown powder; had the highest yield obtained; only required a short purification process (1 hr); and the precipitates could be readily dissolved completely in hot water.

The thus prepared salvianolic acid-gelatin conjugate can be purified using any number of well-known purification techniques, such as by crystallization, solid-liquid extraction, liquid-liquid extraction, membrane filtration, or liquid chromatography.

The salvianolic acid-gelatin conjugate can be coated with the polysaccharide by preparing an aqueous solution of the salvianolic acid-gelatin conjugate and the polysaccharide and adding the thus prepared solution with a liquid solution comprising an organic solvent or an aqueous solution comprising a salt thereby forming the inner shell coated gelatin conjugate.

The salvianolic acid-gelatin conjugate and the polysaccharide can be present in the aqueous solution in a mass ratio of 1:99 to 99:1, respectively. In certain embodiments, the salvianolic acid-gelatin conjugate and the polysaccharide are present in the aqueous solution in a mass ratio of 1:9 to 99:1; 1:4 to 99:1; 3:7 to 99:1; 2:3 to 99:1; 1:1 to 99:1; 3:2 to 99:1; 7:3 to 99:1; 4:1 to 99:1; 9:1 to 99:1, respectively. In certain embodiments, the salvianolic acid-gelatin conjugate and the polysaccharide are present in the aqueous solution in a mass ratio of 1:1 to 9:1; 3:2 to 4:1; 3:2 to 4:1; or 7:3 to 4:1, respectively. In certain embodiments, the salvianolic acid-gelatin conjugate and the polysaccharide are present in the aqueous solution in a mass ratio of 3:1, respectively.

The polysaccharide can be selected from the group consisting of starch, alginic acid, agarose, hyaluronic acid, carboxymethyl cellulose, hydroxypropyl methylcellulose, carrageenan, collagen, dextran, dextran sulfate, chondroitin sulfate, dermatan sulfate, chitin, chitosan, heparan, heparan sulfate, and conjugate salts there and/or combinations thereof.

In certain embodiments, the liquid solution for applying the inner shell is an alkane, aryl solvent (e.g., benzene, toluene, xylenes, or the like), a triglyceride, such as olive oil, sun flower oil, soybean oil, etc, or a combination thereof.

In certain embodiments, the liquid solution for applying the inner shell is an aqueous solution comprising an ammonium salt or a metal salt. In certain embodiments, the metal salt is a Group I or Group II metal salt. The salt can comprise an anion selected from nitrate, halide, phosphate, acetate, or the like. The sale can be present in the aqueous solution at a concentration of 0.01% to 20%; 0.01% to 15%; 0.01% to 10%; 1% to 10%; 1% to 7%; or 2% to 7% m/v. In certain embodiments, the liquid solution is an aqueous solution comprising $CaCl_2$).

The inner shell coated gelatin conjugate can optionally be coated with chitosan, shellac, or an enteric coating material thereby forming the outer shell coating.

The enteric coating material can be Eudragit L-30-D 55 (an anionic copolymer derived from methacrylic acid and ethyl acrylate), hydroxypropyl methylcellulose phthalate HP50 (HPMCP-HP50) (USP/NF 220824), HP55 (HPMCP-HP55) (USP/NF type 200731) and HP55S available from Shin Etsu Chemical, Coateric™ (polyvinyl acetate phthalate) (Colorcon Ltd.), Sureteric™ (polyvinyl acetate phthalate) (Colorcon, Ltd.), or Aquateric™ (cellulose acetate phthalate) (FMC Corp.) and the like.

The outer shell coating comprising chitosan or shellac can be applied in a similar manner as the inner shell coating. More particularly, an aqueous solution comprising the inner shell coated gelatin conjugate and the chitosan or shellac is prepared and the thus prepared aqueous solution is added to a liquid solution comprising an organic solvent or an aqueous solution comprising a salt thereby forming the polymer shell comprising both an inner shell and an outer shell.

The inner shell coated gelatin conjugate and the outer shell coating material can be present in the aqueous solution in a mass ratio of 1:99 to 99:1, respectively. In certain embodiments, the inner shell coated gelatin conjugate and the outer shell coating material are present in the aqueous solution in a mass ratio of 1:9 to 99:1; 1:4 to 99:1; 3:7 to 99:1; 2:3 to 99:1; 1:1 to 99:1; 3:2 to 99:1; 7:3 to 99:1; 4:1 to 99:1; 9:1 to 99:1, respectively. In certain embodiments, inner shell coated gelatin conjugate and the outer shell coating material are present in the aqueous solution in a mass ratio of 1:1 to 9:1; 3:2 to 4:1; 3:2 to 4:1; or 7:3 to 4:1, respectively. In certain embodiments, the inner shell coated gelatin conjugate and the outer shell are present in the aqueous solution in a mass ratio of 3:1, respectively.

In certain embodiments, the liquid solution for applying the chitosan or shellac outer shell is an alkane, aryl solvent (e.g., benzene, toluene, xylenes, or the like), a triglyceride, such as olive oil, sun flower oil, soybean oil, etc, or a combination thereof.

In certain embodiments, the liquid solution for applying the chitosan or shellac outer shell is an aqueous solution comprising an ammonium salt or a metal salt. In certain embodiments, the metal salt is a Group I or Group II metal salt. The salt can comprise an anion selected from nitrate, halide, phosphate, acetate, or the like. The sale can be present in the aqueous solution at a concentration of 0.01% to 20%; 0.01% to 15%; 0.01% to 10%; 1% to 10%; 1% to 7%; or 2% to 7% m/v. In certain embodiments, the liquid solution is an aqueous solution comprising $CaCl_2$).

The enteric coating material can be applied to the inner shell coated gelatin conjugate using well known methods known in the art. The selection of which is well within the skill of an ordinary skill in the art.

The present disclosure also provides a method of treating cancer, inflammatory or a cardiac disease in a subject in need thereof comprising administering a therapeutically effective amount of the nanoparticle described herein to the subject. In certain embodiments, the patient is a human.

The present disclosure is not to be limited in scope by any of the specific embodiments described herein. The specific embodiments described below are presented for exemplification only.

EXAMPLES

Example 1

This example demonstrates the production of a load-retentive hydrogel particle comprising a fluorescein-gelatin conjugate in an alginate hydrogel particle.

The generation of the fluorescein-gelatin conjugate involved the chemical reaction among 0.001 wt./vol. percent of fluorescein, 0.01 wt./vol. percent of gelatin and the cross-linkers, 0.4 wt./vol. percent of 1-ethyl-3-(-3-dimethylaminopropyl) carbodiimide hydrochloride and 0.6 wt./vol. percent of N', N'-dicyclohexyl carbodiimide. The reaction covalently links the carboxylic group of fluorescein with the amino group of gelatin, resulting in the formation of fluorescein-gelatin conjugate. After chemical reaction, 4 parts of ethanol precipitates 1 part of fluorescein-gelatin conjugate to obtain a purified conjugate mixture. A particle mixture containing 1.5 wt./vol. percent of the fluorescein-conjugate, 2 wt./vol. percent of alginate and 98 wt./vol. percent of water formed microsphere upon contact with 5 wt./vol. percent of aqueous calcium chloride.

The stability assessment of the formulations was by visual inspection to detect leakage of fluorescein, whereby the presence of yellowish solution is indicative of instability and, therefore, is considered undesirable, while a clear solution is indicative of a stable formulation. The result showed a clear solution indicative of a stable formulation.

Example 2

This example demonstrates the production of a load-retentive hydrogel particle comprising a salvianolic acid B (SAB)-gelatin conjugate with an agarose hydrogel inner shell core-shell particle.

The generation of the SAB-gelatin conjugate involved the chemical reaction among 0.1 wt./vol. percent of SAB, 0.01 wt./vol. percent of gelatin and the coupling agent, 0.4 wt./vol. percent of 1-ethyl-3-(-3-dimethylaminopropyl) carbodiimide hydrochloride and 0.6 wt./vol. percent of N', N'-dicyclohexyl carbodiimide. The reaction covalently links the carboxylic group of SAB with the amino group of gelatin, resulting in the formation of SAB-gelatin conjugate. After chemical reaction, 4 parts of ethanol precipitates 1 part of SAB-gelatin conjugate to obtain a purified conjugate mixture. The SAB-gelatin conjugate characterized by using ultraviolet-visible (UV-Vis) spectrophotometer revealed the optical spectra of the conjugate. A particle mixture containing 1.5 wt./vol. percent of the conjugate, 0.5 wt./vol. percent of agarose and 98 wt./vol. percent of water formed microsphere upon contact with chilled olive oil.

The stability assessment of the formulations used the following assays: visual inspection to detect leakage of SAB, a UV-Vis spectrophotometric method to measure the SAB-gelatin conjugate in the hydrogel particle after immersion in water. With respect to visual inspection, the presence of dark solution is indicative of instability and, therefore, is considered undesirable, while a clear solution is indicative of a stable formulation. The result showed a clear solution indicative of a stable formulation. With respect to UV-Vis spectrophotometric method, a high quantity of SAB-gelatin conjugate in hydrogel particle is indicative of instability and, therefore, is considered undesirable, while a lower quantity is indicative of a stable formulation. The SAB-gelatin conjugate in hydrogel particle was measured to be high (~80% of the particle weight), indicating a stable formulation (Table 3). As a control, the content of unmodified SAB in hydrogel particle was measured to be below the detection limit of the UV-Vis spectrophotometer, indicating instability.

What is claimed is:

1. A method of preparing a nanoparticle comprising: a core and a polymer shell coating the core, wherein the polymer shell comprises an inner shell comprising at least one polysaccharide and optionally an outer shell comprising chitosan, shellac, or an enteric coating material, wherein the core comprises a salvianolic acid B-gelatin conjugate (SAB-gelatin conjugate) comprising gelatin covalently bonded to salvianolic acid B (SAB), the method comprising:
   contacting gelatin, SAB, a coupling agent, and optionally a coupling additive thereby forming the SAB-gelatin conjugate; coating the SAB-gelatin conjugate with the at least one polysaccharide thereby forming an inner shell coated gelatin conjugate; and optionally coating the inner shell coated gelatin conjugate with chitosan, shellac, or an enteric coating material thereby forming the nanoparticle, wherein the SAB-gelatin conjugate is represented by Formula 1:

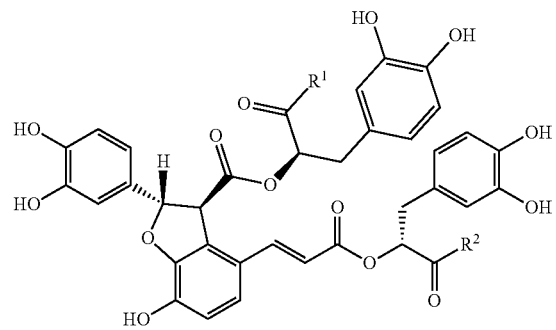

1 or a pharmaceutically acceptable salt thereof, wherein
   $R^1$ and $R^2$ are independently selected from the group consisting of OH and —$NHR^3$; and
   $R^3$ for each instance is independently an amine containing amino acid side chain of the gelatin or a N-terminal amine of the gelatin, with the proviso that at least one of $R^1$ or $R^2$ is —$NHR^3$;
   the at least one polysaccharide is selected from the group consisting of alginate, agarose, hyaluronic acid, carboxymethyl cellulose, hydroxypropyl methylcellulose, and combinations thereof; and
   the enteric coating material is selected from the group consisting of an anionic copolymer derived from methacrylic acid and ethyl acrylate, hydroxypropyl methylcellulose phthalate, polyvinyl acetate phthalate, polyvinyl acetate phthalate, cellulose acetate phthalate, or a combination thereof.

2. The method of claim 1, wherein the coupling agent is 1-ethyl-3-(3-dimethylaminopropyl)carbodiimide (EDC); and the coupling additive is N-hydroxysuccinimide (NHS).

3. The method of claim 1, wherein the gelatin and the SAB are present in a mass ratio between 3:1 to 1:10, respectively.

4. The method of claim 2, wherein the EDC, gelatin and the SAB are present in a mass ratio between 4:3:1 to 40:1:10, respectively.

5. The method of claim 1, wherein the at least one polysaccharide is selected from the group consisting of alginate, agarose, or a combination thereof; and the SAB-gelatin conjugate and the at least one polysaccharide are present in a mass ratio of 1:4 to 99:1, respectively.

6. The method of claim 1, wherein the inner shell coated gelatin conjugate and the chitosan, shellac, or an enteric coating material are present in a mass ratio of 1:4 to 99:1, respectively.

7. The method of claim 4, wherein the at least one polysaccharide is selected from the group consisting of alginate, agarose, or a combination thereof; and the SAB-gelatin conjugate and the at least one polysaccharide are present in a mass ratio of 7:3 to 4:1, respectively.

8. The method of claim 7, wherein the inner shell coated gelatin conjugate and the chitosan or shellac are present in a mass ratio of 7:3 to 4:1, respectively.

\* \* \* \* \*